(12) United States Patent
Janusson et al.

(10) Patent No.: US 6,706,364 B2
(45) Date of Patent: Mar. 16, 2004

(54) COMPOSITE ELASTIC MATERIAL

(75) Inventors: Hilmar Janusson, Seltjarnarnesi (IS); Freygarour Thorsteinsson, Reykjavik (IS); Sigurour A. Asgeirsson, Kopavogur (IS); Palmi Einarsson, Kopavogur (IS)

(73) Assignee: Ossur hf, Reykjavik (IS)

( * ) Notice: Subject to any disclaimer, the term of this patent is extended or adjusted under 35 U.S.C. 154(b) by 135 days.

(21) Appl. No.: 09/805,125

(22) Filed: Mar. 14, 2001

(65) Prior Publication Data

US 2001/0039159 A1 Nov. 8, 2001

Related U.S. Application Data

(60) Provisional application No. 60/189,039, filed on Mar. 14, 2000.

(51) Int. Cl.[7] .............................. A61F 2/78; A61F 2/80
(52) U.S. Cl. ..................... 428/145; 442/59; 442/182; 442/183; 442/306; 428/36.1; 428/36.4; 428/35.7; 623/27; 623/29; 623/32; 623/36
(58) Field of Search .................. 428/145, 36.1, 428/36.4, 35.7, 31.4; 442/59, 182, 183, 306, 187; 623/27, 29, 32, 36, 7; 264/222

(56) References Cited

U.S. PATENT DOCUMENTS

| | | | |
|---|---|---|---|
| 3,634,136 A | 1/1972 | La Habra et al. | |
| 4,463,118 A | * 7/1984 | Evans et al. | 524/264 |
| 4,923,474 A | 5/1990 | Klasson et al. | |
| 5,359,735 A | * 11/1994 | Stockwell | 2/243.1 |
| 5,507,834 A | 4/1996 | Laghi | |
| 5,571,208 A | 11/1996 | Caspers | |
| 5,658,578 A | * 8/1997 | Ogawa et al. | 424/401 |
| 5,728,168 A | 3/1998 | Laghi et al. | |
| 5,733,335 A | * 3/1998 | Ishikawa et al. | 623/7 |
| 5,830,237 A | 11/1998 | Kania | |
| 6,183,766 B1 | 2/2001 | Sine et al. | |

* cited by examiner

Primary Examiner—Terrell Morris
Assistant Examiner—Jennifer Boyd
(74) Attorney, Agent, or Firm—Bacon & Thomas, PLLC

(57) ABSTRACT

A composite elastic material useful for prosthetic applications is constituted of at least one cured silicone elastomer layer containing silicone oil and hollow microspheres dispersed throughout the elastomer layer. An elasticized fabric layer may be intimately bonded to one side of the silicone elastomer layer and the composite elastic material may be incorporated in various prosthetic appliances, including suction liners and sealing sleeves. When used in a suction liner, the composite elastic material may be molded to provide a thicker anterior wall and a thinner posterior wall with a smooth transition between the anterior and posterior walls. The composite elastic material covered with an elasticized fabric may be used as a sealing sleeve between a prosthetic device and a residual limb. The composite elastic material may contain one or more skin treating agents blended into the silicone elastomer.

29 Claims, 4 Drawing Sheets

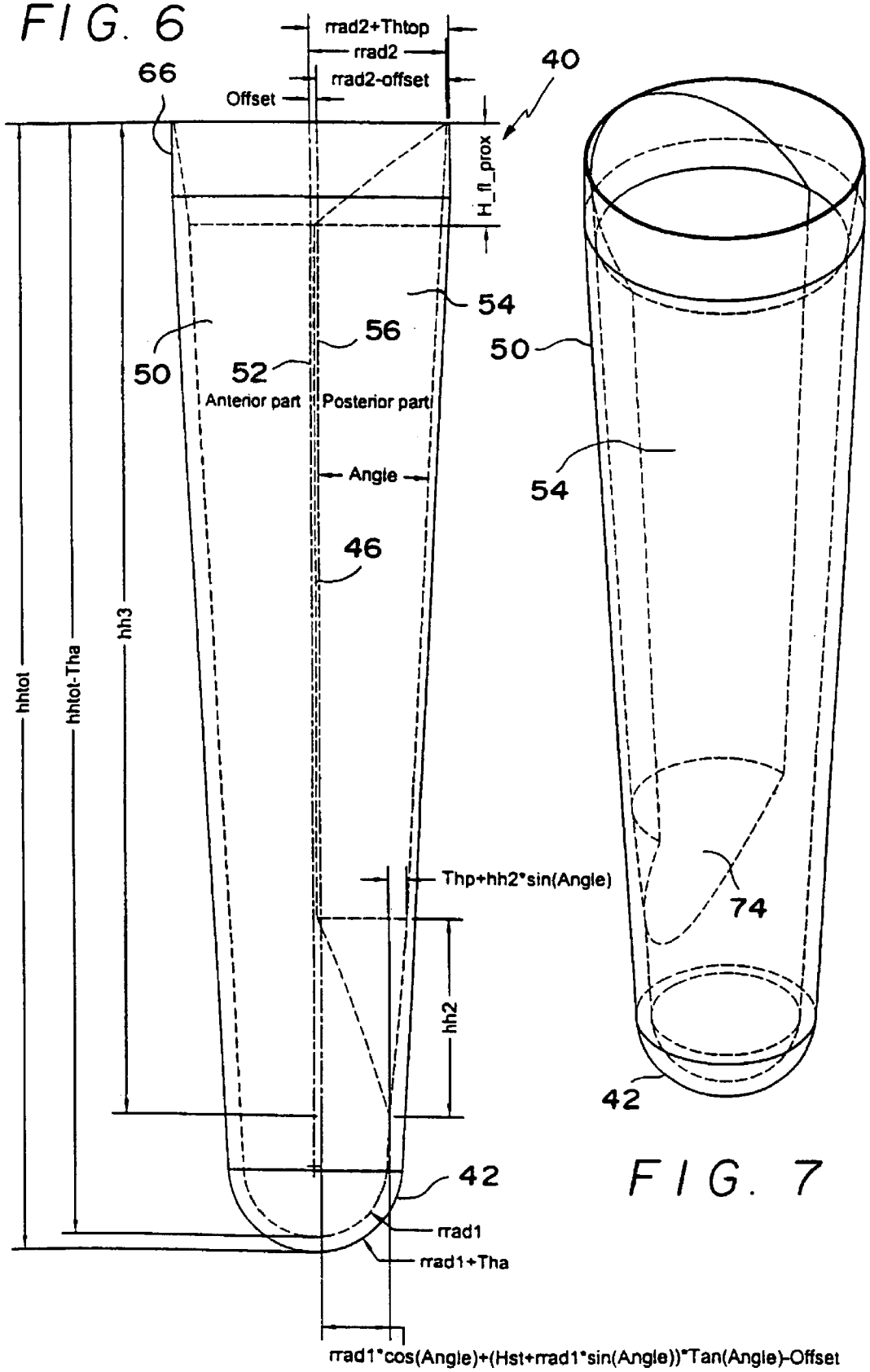

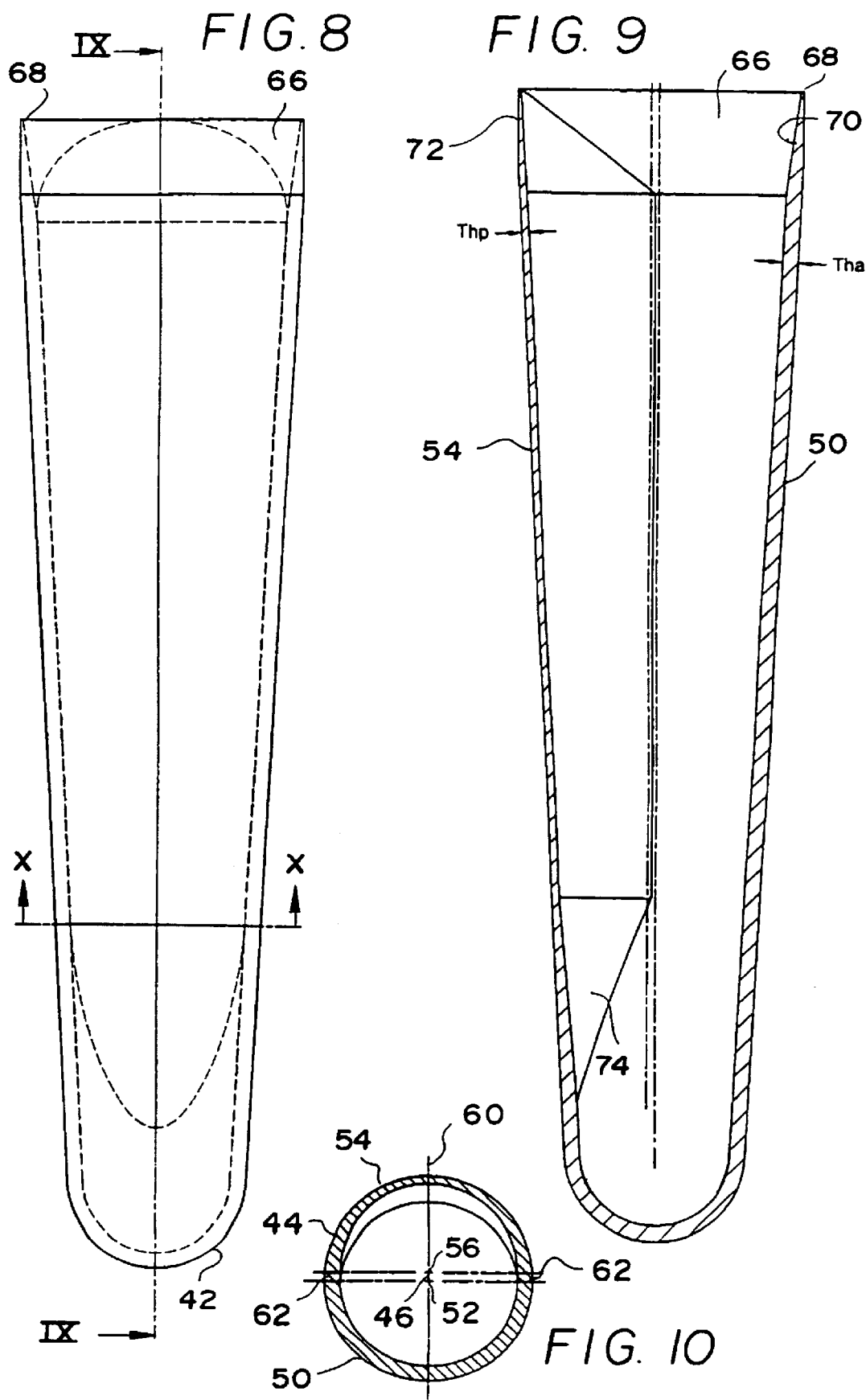

COMPOSITE ELASTIC MATERIAL

CROSS-REFERENCE TO PROVISIONAL APPLICATION

The benefit of Provisional Application No. 60/189,039 filed Mar. 14, 2000 is hereby claimed under 35 U.S.C. §119(e)(1).

FIELD OF THE INVENTION

This invention relates to composite elastic materials useful for prosthetic applications, and prosthetic devices made therefrom.

BACKGROUND OF THE INVENTION

Various silicone elastomer materials have been proposed for use in prosthetic devices such as suction liners of the type described in U.S. Pat. No. 4,923,474 granted to Klasson and Kristinsson on May 8, 1990. Other examples of such suction liners include U.S. Pat. No. 5,728,168 granted Mar. 17, 1998 to Laghi et al. and U.S. Pat. No. 5,830,237 granted to Kania Nov. 3,1998.

Composite elastomer materials useful for both suction liners and sealing sleeves are disclosed in U.S. Pat. No. 5,571,208 granted Nov. 5,1996 to Caspers.

It is highly desirable to provide a relatively soft cushion in contact with or adjacent the skin of the user of a prosthetic device for comfort. However, the cushion must be relatively inert with respect to the skin of the user, be readily washable and feel comfortable. Silicone elastomers and silicone gels are generally known for such applications and function satisfactorily as suction liners in sleeves both when the silicone material is used alone and when it is used in combination with an outer stretchable fabric covering.

It has been observed, however, that as the thickness of the silicone elastomer cushion grows, so does the weight of the suction liner. It is highly desirable to obtain the soft cushioning effect of a silicone elastomer in a suction liner application while reducing the overall weight of the liner attributable to the silicone elastomer.

In suction sleeves formed with a silicone elastomer liner, it is desirable to form a relatively thin posterior wall and a relatively thick anterior wall to provide cushioning on the anterior wall while avoiding interference with movement of the prosthetic user, particularly with a below-the-knee amputee. Such a configuration, on the other hand, generally requires a discontinuity of curvature in the transition regions between the anterior and posterior walls. This rapid transition in wall thickness and curvature can be a source of discomfort to a prosthetic user and it is desirable to avoid such rapid change in elastomer wall thickness in these transition regions.

BRIEF SUMMARY OF THE INVENTION

The present invention is a composite elastic material particularly useful for prosthetic applications and that is formed of at least one cured silicone elastomer layer containing silicone oil and hollow microspheres dispersed throughout the elastomer layer.

The composite elastic material preferably also includes an elasticized fabric layer intimately bonded to one side of the silicone elastomer layer described above.

The composite elastic material may be used in the form of a tubular prosthetic suction liner having a closed distal end and dimensioned and configured so as to be rollable onto a distal end of a residual limb of a prosthetic device user, with a silicone elastomer layer on the interior of the liner and the elasticized fabric on the exterior of the liner. Such residual limb receiving liners are used between a socket of a prosthetic appliance and the residual limb of the appliance user.

The composite elastic material also may be used as a sealing sleeve that is tubular in form and open at opposed ends, with the silicone elastomer layer covering the inside wall of the sleeve and the elasticized fabric covering the exterior of the sleeve. Such a sleeve is dimensioned and configured to be installed as a suction seal between a prosthetic device and the residual limb of the prosthetic device user, with the silicone elastomer layer facing towards the location of the residual limb with the upper end of the prosthetic device located within the sleeve.

When used in a suction liner, the composite elastic material may include a distension controlling reinforcement matrix embedded in the silicone elastomer layer over a distal end area of the suction liner, wherein the reinforcement matrix, for example a circular knit textile, contains reinforcement elements that provide substantial stiffness against elongation of the liner in a direction along the liner length but which do not provide substantial resistance against distension of the silicone elastomer layer in directions transverse to the liner length.

A rigid prosthetic connector element may be attached to the distal end of the suction liner by embedding the connector element in a cured silicone elastomer distal end cap adhered to the distal end of the suction liner. The connector is sufficiently exposed while embedded in the end cap so as to provide access to a prosthetic connector pin that may be fastened to the connector. The silicone elastomer distal end cap may be formed of a silicone elastomer having a higher durometer than the composite elastic silicone elastomer layer to provide a more rigid support zone at the distal end of the suction liner.

The microspheres used in the composite elastic material preferably are expanded polymeric shells having a density of 0.005 g/cm$^3$ to 1.25 g/cm$^3$, preferably 0.05 g/cm$^3$.

The silicone elastomer layer preferably comprises, by weight, 50–99.4% silicone elastomer; 0.5–45% silicone oil; and 0.1–5% microspheres. Preferably, the ratio of silicone elastomer, silicone oil and microspheres is: 77.25% silicone elastomer; 10% silicone oil and 0.75% microspheres (by weight).

Preferably, the silicone elastomer material of the composite elastic material is blended with one or more skin treating agents such as Vaseline (Petroleum jelly) and aloe Vera. For example, the silicone elastomer may be blended with up to 3% aloe vera by weight of the silicone elastomer layer, with the balance of the skin treatment agent constituting Vaseline, so that the silicone elastomer layer is blended with skin treatment agents up to about 20% by weight of the silicone elastomer layer.

The composite elastic material containing silicone elastomer, silicone oil, and microspheres preferably has a density of 0.5 g/cm$^3$ to 1.3 g/cm$^3$; a tensile strength of at least 0.1 Pa; a durometer (00) of 13–62; a 100% modulus of 5 kPa to 250 kPa; and a compression set of 0 to 30.

The invention also contemplates a suction liner formed of the composite elastic material in accordance with the invention wherein the suction liner is tapered conically inwardly towards its distal end from its open proximal end, and wherein the sleeve has a circular outer wall having radii of curvature centered along a first longitudinal sleeve axis of external symmetry extending longitudinally centrally within the sleeve, a circular curved inside anterior wall portion extending along a sleeve length and having first radii of curvature centered on a second longitudinal axis of anterior curvature extending longitudinally along said sleeve length and a circular curved inside posterior wall portion having second radii of curvature centered on a third longitudinal axis of posterior curvature extending along said sleeve length; said first, second and third longitudinal axes lying in a common longitudinally and transversely extending plane bisecting the anterior and posterior wall portions, and wherein said second and third axes are spaced apart at predetermined offset distance on opposed sides of said first axis to thereby define an anterior wall portion that is thicker along the sleeve length than the posterior portion; and further wherein the anterior and posterior wall portions intersect each other along said sleeve length on the sleeve interior along diametrically opposed inner transition wall portions that extend tangentially relative to the adjoining anterior and posterior wall portions along said sleeve length, whereby the interior wall of the suction sleeve along the transition wall portions is free of rapid changes in thickness, curvature or cross-section profile.

Preferably, the second and third radii of curvature are equal to each other along their respective second and third axes.

A spherical curved inside distal wall portion may be provided within the suction liner, said distal wall portion joining the adjoining interior wall of the suction liner along a tangency that forms a smooth transition between the inside distal wall portion and the adjoining interior wall of the suction liner. The thickness of the adjacent interior wall of the suction liner may be the same as the thickness of the anterior wall of the suction liner.

When provided with an elasticized fabric layer bonded on one side of the silicone elastomer layer, a thin continuous coating of second cured elastomer material is provided on the elasticized fabric between the fabric and the principal silicone elastomer layer. The thin coating of the second elastomer material partially penetrates and is embedded in the fabric layer and forms a continuous coating over the textile material between the textile and the principal silicone elastomer layer. The silicone elastomer coating material is fully stretchable elastically at least to same extent as the elasticized fabric layer to which it is attached and adhered.

When the composite elastic material is formed into a sealing sleeve with an elasticized textile fabric layer bonded on one side of the silicone elastomer layer, the textile fabric may be a circular rib knit formed principally of Nylon with a small amount of Lycra (a fiber available from DuPont) or other stretchable fiber. A secondary coating of cured silicone elastomer material may be used between the principal silicone elastomer layer and the fabric, in the same manner as described above.

BRIEF DESCRIPTION OF THE DRAWINGS

With reference to the appended drawings which illustrate preferred embodiments of the invention:

FIG. 6 is a side elevational view of another example of a suction liner made with a composite elastic material in accordance with the present invention;

FIG. 7 is an isometric view of the suction liner shown in FIG. 6;

FIG. 8 is a front elevation view of the suction liner shown in FIG. 6;

FIG. 9 is a section view taken along line IX—IX of FIG. 8; and

FIG. 10 is a section view taken along line X—X of FIG. 8.

DETAILED DESCRIPTION OF PREFERRED EMBODIMENTS OF THE INVENTION

Figure 1:
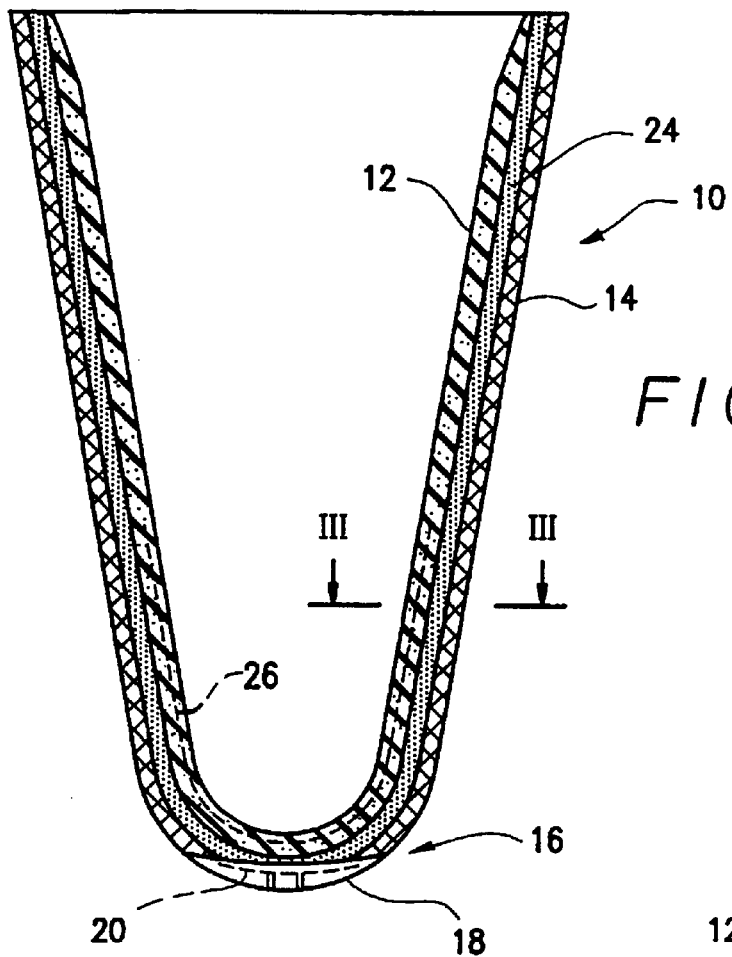
FIG. 1 is a cross-section of a suction liner constructed in accordance with the present invention and utilizing a composite elastic material also made in accordance with the invention.

FIG. 1 schematically illustrates in a cross-section view a prosthetic suction liner 10 formed in part of a composite elastic material 12 on its interior surface and an elasticized fabric layer 14 on its exterior surface at least up to its distal end area 16, where a distal end cap 18 having embedded therein a rigid prosthetic connector 20 formed, for example, of aluminum or other metal, or rigid plastic such as Nylon.

The liner 10 is formed as a close ended tapered tubular element, as is conventional for such suction liners. The distal end cap 18 firmly joins the prosthetic connector 20 to the suction liner 10 while providing a cushioning and stabilizing surface at the distal end of the liner. The prosthetic connector 20 includes preferably a threaded aperture 22 for providing access to a threaded prosthetic pin connector in a manner well known in the art.

Figure 2:
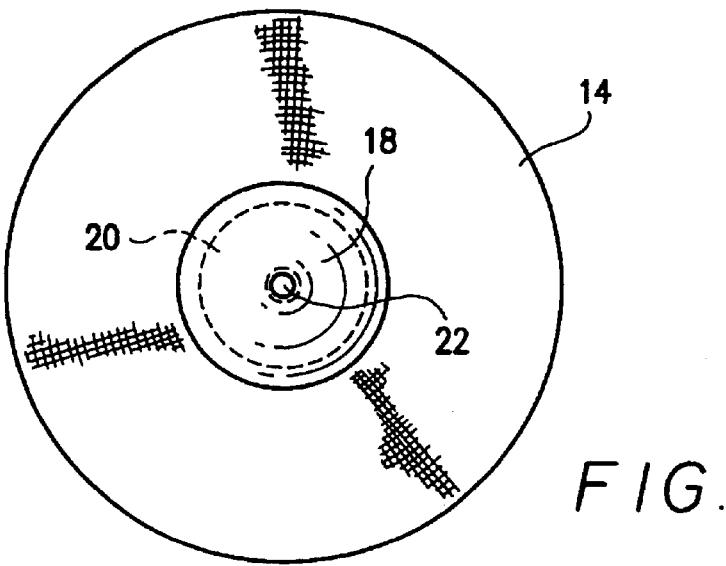
FIG. 2 is a distal end view of the suction liner shown in FIG. 1.

FIG. 2 shows the suction liner in an end view as seen from the distal end of the liner.

Figure 3:
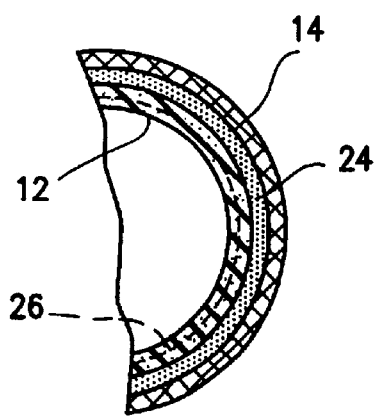
FIG. 3 is a section taken along line III—III of FIG. 1.

FIG. 3 is a cross-section view taken along line III—III of FIG. 1 and shows the composite elastic material 12, the elasticized fabric layer 14, and a second thin continuous coating of silicone elastomer material 24 partially embedded in the elasticized fabric layer 14 while not completely penetrating the fabric layer. The intermediate coating 24 is bonded on its opposite side to the composite elastic material 12, whereby the entire assembly of composite elastic material 12, elastomer coating 24 and elasticized fabric 14 is at least freely radially elastically distendable.

The composite elastic material layer 12 may have embedded therein a matrix of fibers 26 or other suitable stiffness reinforcement having properties such that the composite elastic layer 12 is rendered relatively stiff against longitudinal elongation while it is freely distendable radially of the suction liner for use in liner applications when axial elongation of the liner must be limited.

Figure 4:
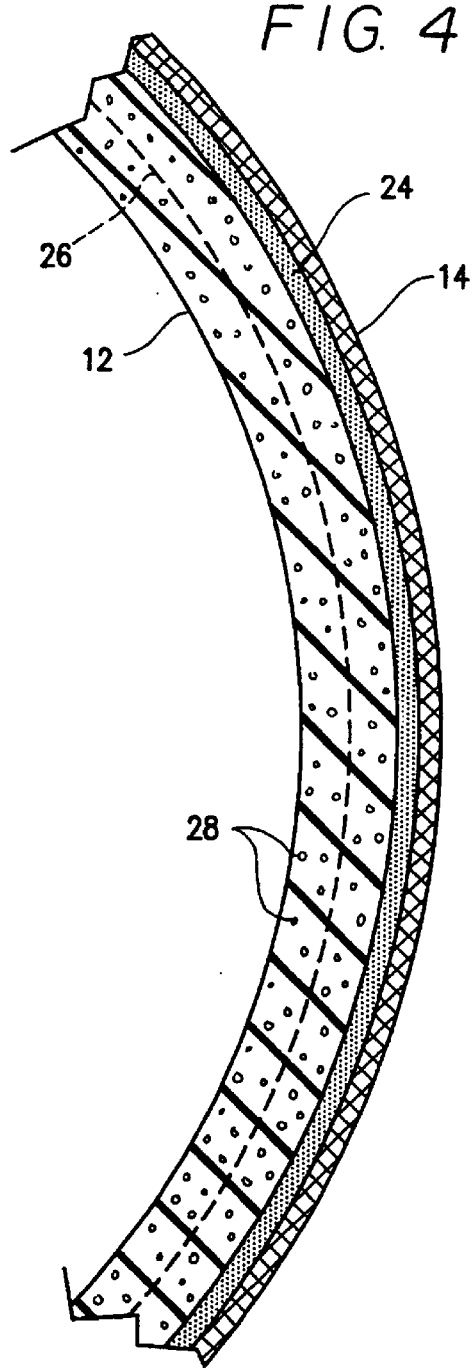
FIG. 4 is an enlarged view of FIG. 3.

FIG. 4 is an enlarged view of FIG. 3 and shows the composite elastic material made in accordance with the present invention in more detail as well as the wall section of a suction liner 40 made with such material. Layer 12 is the composite elastic material comprising a cured silicone elastomer containing silicone oil and hollow microspheres 28 dispersed throughout the silicone elastomer layer.

The illustrations in FIGS. 3 and 4 also show the reinforcement fibers 26 embedded in the silicone elastomer layer, but it should be understood that such reinforcement fibers are optional and extend over a distal portion of the liner to limit axial distension of the liner in such distal portion. The reinforcement fibers 26, of course, do not constitute a portion of the basic composite elastic material described above.

More specifically, the composite elastic material layer 12 itself is regarded as a new and useful composite elastic material independently of the fibers 28, the outer fabric 14 and the intermediate coating.

In a preferred example, the composite elastic material 12 is formed principally of a silicone elastomer obtainable from NuSil Technology of Carpinteria, Calif. under Product Designation CF13-2188. For a fuller description of the silicone material, reference may be made to U.S. Pat. No. 6,136,039 granted Oct. 24, 2000, owned by the assignee of the invention described herein.

Embedded within the silicone elastomer material of layer 12 are hollow thermoplastic microspheres consisting of a polymeric shell with an enclosed blowing agent. The specific thermoplastic microspheres utilized in this example of the invention are expanded microspheres obtained from AKZO NOBEL of Sweden under the trade name EXPANCEL®, Product No. 551DE.

The microspheres 28 preferably have a density of 0.005 g/cm$^3$ to 1.25 g/cm$^3$, preferably 0.05 g/cm$^3$.

For a fuller understanding of the formulation of EXPANCEL® microspheres, reference may be made to EXPANCEL® Technical Bulletin 29 and the EXPANCEL® product specification and material safety data sheets, all available from AKZO NOBEL, S-850, 13, Sundsvall, Sweden.

The silicone oil included in the composite elastic material may be obtained from GE Bayer Silicones GmbH of DJ1 368 Leverkusen, Germany under Product Name Baysilone Fluid M350.

In a preferred form, the composite elastic layer 12 comprises 50–99.4% by weight of silicone elastomer, preferably 77.25%; 0.5–45% by weight of silicone oil, preferably 10%; and 0.1–5% by weight of microspheres, preferably 0.75%.

The composite elastic layer 12 also may include one or more skin treatment agents blended into the silicone elastomer, for example Vaseline or petroleum jelly and aloe vera. In a preferred example, up to 20% by weight of the composite elastic layer, preferably 11.9%, may be Vaseline and up to 3%, preferably 0.1%, may be a secondary skin treatment agent such as aloe vera.

While EXPANCEL® hollow microspheres as described above are preferred, it should be understood that other hollow microspheres having a density range of 0.005 g/cm$^3$ to 1.24 g/cm$^3$, preferably 0.05 g/cm$^3$, could be used.

When prepared as described above, a preferred embodiment of the composite elastic layer will have a density of 0.5 g/cm$^3$ to 1.3 g/cm$^3$, preferably 0.94 g/cm$^3$; a tensile strength greater than 0.1 Pa, preferably greater than 0.5 Pa; a durometer (00) of 13 to 62, preferably 22; a 100% modulus of 5 kPa to 250, preferably 20 kPa; and a compression set of 0 to 30, preferably 8.

It should be understood that different or additional skin treating agents may be utilized, depending upon the skin condition to be treated by the skin treating agent. For use as a typical suction sleeve, Vaseline and aloe vera are believed to provide good properties for the composite elastic layer that typically directly contacts or is in close proximity with the skin of a prosthetic user.

When the composite elastic material 12 is laminated or bonded with an elasticized textile layer 14, such layer 14, in a preferred embodiment, may be described as a Supplex Nylon circular knit of 87% Nylon, 13% Spandex fibers using 28 needles per 2.5 cm having a weight per square yard of 6.9 ozs. and a weight per linear yard of 12 ozs. Such a Supplex Nylon is obtainable from Agmont Inc. of Montreal, Quebec, Canada under Style Name 5095. This material has a finished width of 60" (152.4 cm) and is substantially elastically distendable along its length and width in a manner appropriate for a prosthetic suction liner.

The reinforcing fibers 26 may be a circular knit textile formed of relatively non-distendable fibers (at least within the load ranges contemplated for use in a prosthetic suction liner) wherein the knit construction is such that the layer 26 strongly resists elongation in a longitudinal direction while being freely distendable laterally in a radial direction when it is embedded in the composite elastic layer 12. Any appropriate reinforcement matrix that would provide such properties could be used for layer 26, but as a practical matter a circular knit glass fiber or Nylon material is appropriate, provided it has the anisotropic properties described above.

The textile layer 14 is normally air permeable and is usually formed from a flat knit elasticized fabric that has been rolled into a tube and stitched along abutting side edges along the length of the tube. The inside surface of the fabric layer 14 facing the composite elastic layer 12 is coated with a thin layer of cured silicone elastomer 24 that is partially embedded in the fibers of the textile 14 without completely penetrating the textile 14. The silicone elastomer layer 24 is cured while embedded in the textile so that it is firmly adhered to the textile and preferably renders the textile and silicone layer 24 impermeable to air. The thin coating of silicone elastomer 24 provides a good bonding surface for the composite elastic layer 12 described above.

Preferably, the silicone layer 24 is obtainable under Product No. CF15-2188 from NuSil Technology of Carpinteria, Calif. Physical properties of the combined composite elastic layer 12, coating 24 and elasticized fabric 14 include a tensile strength greater than 1 Pa, preferably greater than 2 Pa; and a 100% modulus of 5 to 300 kPa, preferably 55 kPa.

The distal end cap 18 may be formed of a silicone elastomer including 98% by weight silicone rubber, type MED-4950 or type MED-4050 or type CF15-2188, all available from NuSil Technology, with the balance (2%) constituted of a color mixture, for example a color powder blended from 12.5 parts Lucas color No. 2408, 12.5 parts Lucas color No. 2439 and 75 parts Lucas color No. 2510 all obtainable from Fr. Schoenfeld GmbH and Co. Further properties of MED-4950 as published by NuSil Technology include: the material uses a platinum cure system; a press cure time of 50 minutes at 150° C.; durometer 45–55; tensile strength 1000 psi (6.9 MPa); elongation 400%; and a tear strength 230 ppi (40.3 kN/M).

Figure 5:
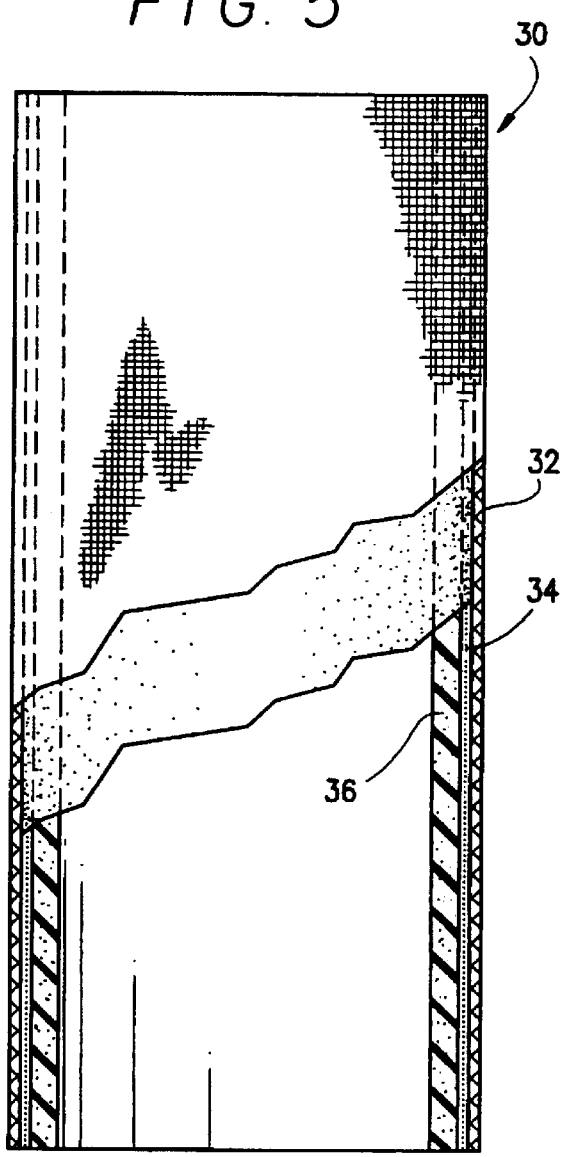
FIG. 5 illustrates a sealing liner made with a composite elastic material in accordance with the present invention.

As illustrated in FIG. 5, a sealing sleeve 30, for example a sleeve capable of sealing the gap between the upper end of a prosthetic socket and a residual limb as illustrated in U.S. Pat. No. 5,571,208 includes an outer textile layer 32 that is an elasticized, porous or air permeable fabric on which a continuous cured silicone coating 34 has been applied and bonded thereto in the same manner as the coating 24 attached to the layer 14 of the suction sleeve material as illustrated in FIGS. 1–4 and described above.

The interior surface of the sleeve 30 includes a composite elastic material 36 formed in the same manner as the composite elastic layer 12 illustrated in FIGS. 1–4 and described above. The thickness of the composite elastic material 36 may be adjusted to fit the requirements of a sealing sleeve. The composite elastic layer 36 is intimately bonded and adhered to the coating 34. The combined assembly of the textile 32, coating 34 and composite elastic layer 36 is fully distendable both radially and longitudinally in accordance with the requirements of a sealing sleeve for prosthetic applications.

The outer fabric layer 32, in a preferred embodiment, may be a circular rib knit fabric made of 95% Nylon and 5% Lycra (a synthetic fiber product made by DuPont), knit as a 1×1 rib using 220 needles per 2.5 cm for a 12 cm width tube and 264 needles per 2.5 cm for a 14 cm tube. This fabric may be obtained from RX-Textile of Monroe, N.C.

A preferred formed of the suction liner made with the composite elastic material layer 12 is illustrated in FIGS. 6–10 (the fabric is omitted in the veiws as being nonessential). The composite elastic material including the cured silicone elastomer layer with silicone oil and hollow microspheres and outer fabric is molded or formed as a tapered suction liner 40 having a closed distal end 42 of uniform thickness, an external profile 44 (see FIG. 10) that is circular with the radii of curvature of the external surface 44 centered on a first central longitudinal axis 46 extending through the suction liner 40. The geometry of such suction liner is illustrated in FIGS. 6–10. Moreover, the following table 1 describes the variables shown in FIGS. 6–10 and also describes typical values of some of the variables for different size suction liners listed in the left column of the table entitled "Typical Values of Variables".

TABLE 1

VARIABLE DESCRIPTION

| Variable name | Description |
|---|---|
| Angle | Angle of socket opening |
| H_fl_prox | Height of flange in proximal area |
| HH1 | Height to flange in distal area |
| HH2 | Height of flange in distal area |
| HH3 | Height of second cut |
| HHtot | Total height of socket |
| Hst | Height from radius to start of distal flange |
| Offset | Offset in lathe |
| Rrad1 | Radius on Distal end |
| RRad2 | Radius on proximal end |
| Tha | Thickness in anterior area |
| Thp | Thickness in posterior area |
| Thtop | Thickness of socket in top |

The suction liner 40 includes a circular curved inside anterior wall portion 50 having first radii of curvature centered on a second longitudinal axis of anterior curvature 52 extending longitudinally through the suction sleeve towards the anterior side of the first central axis 46 and a posterior wall portion 54 having second radii of curvature centered on a third longitudinal axis 56 located in the posterior direction relative to the central axis 46, said first, second and third longitudinal axes 46, 52 and 56 all lying in a common longitudinally and transversely extending imaginary plane 60 (FIG. 10) bisecting the anterior and posterior wall portions 50, 54 and wherein the second and third axes 52 and 56 are spaced apart at predetermined offset distance from each other on opposed sides of the first axis 46. Thus, this arrangement produces a posterior wall that is thinner than the anterior wall as shown in FIG. 10.

The anterior and posterior wall portions 50, 54 intersect each other along inner diametrically opposed transition wall portions 62 that extend tangentially relative to the adjoining anterior and posterior wall portions along the sleeve length, so that the interior wall surface of the suction liner along the transition areas 62 are free of rapid changes in thickness, curvature or cross-section profile, as seen best in FIG. 10.

In the example illustrated, the radii of curvature of the inside surfaces of the anterior and posterior portions of the sleeve are equal to each other along their respective second and third axes, as observable in FIG. 10. A formula for generating the interior profile of the suction sleeve shown in FIGS. 6–10 is indicated at the bottom of FIG. 6, and such formula is used to control a computer assisted machine tool (e.g., lathe) used to form a male mold element that shapes the inner profile of the liner.

At the proximal area of the suction liner 40 (the open end of the sleeve) a flange area 66 is provided wherein the thickness of the composite elastic material progressively thins as the top edge 68 is approached. The inside surface of the flange portion 66 of the anterior wall 50, as seen in FIG. 9, tapers inwardly as the top edge 68 is approached as shown at 70 and the outer surface of the proximal end of the flange portion 66 of posterior wall 54 also tapers inwardly as shown at 72 in FIG. 9. Preferably, the top edge 68 of the sleeve is relatively thin as compared with the thickness of the remainder of the sleeve.

TYPICAL VALUES OF VARIABLES

| Size | Rrad1 | HH1 | HH2 | HH3 | Hhtot | RRad2 | Tha | Angle | Hfh prox | Offset | Thp | Hst | Thtop |
|---|---|---|---|---|---|---|---|---|---|---|---|---|---|
| 12 | 19 | rrad1 + Hst | 80 | Hhtot-HH1-Tha | 450 | 44.1 | 6 | 3 | 40 | 3 | 3 | 20 | 1 |
| 14 | 22.5 | rrad1 + Hst | 80 | Hhtot-HH1-Tha | 450 | 48.1 | 6 | 3 | 40 | 3 | 3 | 20 | 1 |
| 16 | 25.5 | rrad1 + Hst | 80 | Hhtot-HH1-Tha | 450 | 51 | 6 | 3 | 40 | 3 | 3 | 20 | 1 |
| 18 | 28.5 | rrad1 + Hst | 80 | Hhtot-HH1-Tha | 450 | 53.8 | 6 | 3 | 40 | 3 | 3 | 20 | 1 |
| 20 | 31.5 | rrad1 + Hst | 80 | Hhtot-HH1-Tha | 450 | 56.7 | 6 | 3 | 40 | 3 | 3 | 20 | 1 |
| 21 | 33.5 | rrad1 + Hst | 80 | Hhtot-HH1-Tha | 450 | 58.6 | 6 | 3 | 40 | 3 | 3 | 20 | 1 |
| 22 | 35.5 | rrad1 + Hst | 80 | Hhtot-HH1-Tha | 450 | 60.5 | 6 | 3 | 40 | 3 | 3 | 20 | 1 |
| 23.5 | 37.5 | rrad1 + Hst | 80 | Hhtot-HH1-Tha | 450 | 62.4 | 6 | 3 | 40 | 3 | 3 | 20 | 1 |
| 25 | 40 | rrad1 + Hst | 80 | Hhtot-HH1-Tha | 450 | 64.7 | 6 | 3 | 40 | 3 | 3 | 20 | 1 |
| 26.5 | 42.5 | rrad1 + Hst | 80 | Hhtot-HH1-Tha | 450 | 67.1 | 6 | 3 | 40 | 3 | 3 | 20 | 1 |
| 28 | 45 | rrad1 + Hst | 80 | Hhtot-HH1-Tha | 450 | 69.5 | 6 | 3 | 40 | 3 | 3 | 20 | 1 |
| 30 | 48 | rrad1 + Hst | 80 | Hhtot-HH1-Tha | 450 | 72.3 | 6 | 3 | 40 | 3 | 3 | 20 | 1 |
| 32 | 51 | rrad1 + Hst | 80 | Hhtot-HH1-Tha | 450 | 75.1 | 6 | 3 | 40 | 3 | 3 | 20 | 1 |
| 34 | 54 | rrad1 + Hst | 80 | Hhtot-HH1-Tha | 450 | 78 | 6 | 3 | 40 | 3 | 3 | 20 | 1 |
| 36 | 57 | rrad1 + Hst | 80 | Hhtot-HH1-Tha | 450 | 80.8 | 6 | 3 | 40 | 3 | 3 | 20 | 1 |
| 38 | 60.5 | rrad1 + Hst | 80 | Hhtot-HH1-Tha | 450 | 84.2 | 6 | 3 | 40 | 3 | 3 | 20 | 1 |
| 40 | 64 | rrad1 + Hst | 80 | Hhtot-HH1-Tha | 450 | 87.5 | 6 | 3 | 40 | 3 | 3 | 20 | 1 |
| 42.5 | 67.5 | rrad1 + Hst | 80 | Hhtot-HH1-Tha | 450 | 90.8 | 6 | 3 | 40 | 3 | 3 | 20 | 1 |
| 45 | 71.5 | rrad1 + Hst | 80 | Hhtot-HH1-Tha | 450 | 94.6 | 6 | 3 | 40 | 3 | 3 | 20 | 1 |

The distal end 42 of the sleeve is spherical in curvature and joins the adjoining side wall of the sleeve along a tangent so as to provide a smooth interior and exterior contour as the sleeve transitions between the tapered conical upper portion and the spherically curved closed end portion 42. The thickness of the end portion 42 may be the same thickness as the anterior wall 50. The posterior wall 54 transitions from the same thickness as the anterior wall at the distal end of the sleeve to a thinner wall section over the length of the sleeve in which the thinner wall section is desired. A smooth transition area 74 is provided between the thinner posterior wall section 54 and the full thickness of the wall portion of the sleeve at the distal end of the sleeve.

The invention is not limited to the specific embodiments and examples described herein, but rather extends to the full scope of the disclosure, drawings and claims hereof as well as variations thereof that may be readily apparent to a person skilled in the art and which would constitute the equivalents of the disclosed elements described herein.

I claim:

1. A composite elastic material useful for prosthetic applications, comprising:
   at least one cured silicone elastomer layer containing silicone oil;
   hollow microspheres dispersed throughout the elastomer layer, wherein said composite elastic material is in the form of a tubular prosthetic suction liner having a closed distal end, and configured so as to be rollable onto a distal end of a residual limb of a prosthetic device user.

2. A composite elastic material useful for prosthetic applications, comprising:
   at least one cured silicone elastomer layer containing silicone oil;
   hollow microspheres dispersed throughout the elastomer layer;
   an elasticized fabric layer intimately bonded to one side of the silicone elastomer layer; wherein said composite elastic material is in the form of a tubular sleeve open at opposed ends with the silicone elastomer layer covering the inside wall of the sleeve and the elasticized fabric covering the exterior of the sleeve.

3. The composite elastic material as claimed in claim 1, including an elasticized fabric layer intimately bonded to one side of the silicone elastomer layer.

4. The composite elastic material as claimed in claim 3, including a distension controlling reinforcement matrix embedded in the silicone elastomer layer over a distal end area of the suction liner, said matrix containing reinforcement elements that provide substantial stiffness against elongation of the liner in a direction along the liner length and which do not provide substantial resistance against distension of the silicone elastomer layer in directions transverse to the liner length.

5. The composite elastic material as claimed in claim 3, wherein said reinforcement matrix is a knit textile having anisotropic distension properties along orthogonal directions, such that the textile is relatively inextensible in a first direction and is relatively freely extensible in an orthogonal direction.

6. The composite elastic material as claimed in claim 1, including a rigid prosthetic connector element attached to the distal end of said liner, said connector element arranged to engage and retain a prosthetic pin connector usable by a prosthetic user, said connector element embedded in a cured silicone elastomer distal end cap adhered to the distal end of said suction liner and providing access to a prosthetic pin connector.

7. The composite elastic material as claimed in any one of claims 3, 4, 5, or 6, wherein said suction liner is tapered inwardly towards its distal end, and wherein the liner has a circular outer wall having radii of curvature centered along a liner first longitudinal axis of external symmetry extending longitudinally centrally within the liner; a circular curved inside anterior wall portion extending along a liner length, and having first radii of curvature centered on a second longitudinal axis of anterior curvature extending longitudinally along said liner length and a circular curved inside posterior wall portion having second radii of curvature centered on a third longitudinal axis of posterior curvature extending along said liner length, said first, second and third longitudinal axes lying in a common longitudinally and transversely extending plane bisecting the interior and posterior wall portions, and wherein said second and third axes are spaced apart a predetermined offset distance on opposed sides of said first axis to thereby define an interior wall portion that is thicker along said liner length than the posterior portion; and further wherein said anterior and posterior wall portions intersect each other along said liner length on the liner interior along diametrically opposed inner transition wall portions that extend tangentially relative to the adjoining anterior and posterior wall portions along said liner length, whereby the interior wall of the suction liner along the inner transition wall portions are free of rapid changes in thickness, curvature or cross-section profile.

8. The composite elastic material in claim 7, wherein said second and third radii are equal to each other along their respective second and third axes.

9. The composite elastic material as claimed in claim 7, wherein an interior proximal flange area of said interior wall portion is tapered radially outwardly and an exterior proximal flange area of said posterior wall portion is tapered radially inwardly.

10. The composite elastic material as claimed in claim 7, including a spherical curved inside distal wall portion of said suction liner, said distal wall portion joining the adjoining interior wall of the suction liner along a tangency that forms a smooth transition between the inside distal wall portion and the adjoining interior wall of the suction liner, and further wherein the adjoining wall of the suction liner is circular in cross-section and has a center of curvature located on said first axis; and further wherein the thickness of the wall of the suction liner adjoining said spherical curved distal wall portion is uniform and equal to the thickness of said anterior wall portion.

11. The composite elastic material as claimed in one of claims 1, 2, 3, 4, 5 or 6 including a second cured silicone elastomer layer between the at least one silicone elastomer layer and the elasticized fabric layer, said second silicone elastomer layer partially penetrating and being embedded in said textile layer on one side thereof so as to form a continuous coating on said one side, and adhered to said at least one silicone elastomer layer on the opposite side of the second silicone elastomer layer.

12. The composite elastic material as claimed in claim 2, wherein said elasticized fabric layer is a normally porous, air permeable material that has been rendered non-air permeable by a second silicone cured elastomer layer, said second silicone elastomer layer forming a relatively thin coating as compared with the elasticized fabric layer on said one side of said fabric layer.

13. The composite elastic material as claimed in claim 1, 2, 3, 4, 5 or 6, wherein the composite elastic material has a minimum tensile strength of one Pa and a 100% modulus of 5 to 30 kPa.

14. The composite elastic material as claimed in claim 13, wherein the elasticized fabric is supplex Nylon jersey knit, 28 needles per 2.5 cm, comprising 87% Nylon, 13% Spandex, said fabric substantially stretchable beyond its relaxed dimensions both lengthwise and widthwise.

15. The composite elastic material as claimed in claim 1, 2, 3, 4, 5 or 6, wherein said microspheres are expanded polymeric shells.

16. The composite elastic material as claimed in claim 1, 2, 3, 4, 5 or 6, wherein said microspheres have a density of 0.005 to 1.25 g/cm$^3$.

17. The composite elastic material as claimed in claim 16, wherein said microspheres have a density of 0.05 g/cm$^3$.

18. The composite elastic material as claimed in claim 1, 2, 3, 4, 5 or 6, wherein said at least one silicone elastomer layer comprises, by weight:

50–99.4% silicone elastomer 0.5–45% silicone oil 0.1–5% microspheres.

19. The composite elastic material as claimed in claim 18, wherein the ratios of silicone elastomer, silicone oil and microspheres are as follows, by weight:

77.25% silicone elastomer

10% silicone oil 0.75% microspheres.

20. The composite elastic material as claimed in any one of claims 1–6, including one or more skin treatment agents blended with the silicone elastomer.

21. The composite elastic material as claimed in claim 20, wherein the skin treatment agent consists of petroleum jelly, said petroleum jelly present in an amount of up to 15% by weight of the silicone elastomer layer.

22. The composite elastic material as claimed in claim 20 wherein the skin treatment agent comprises petroleum jelly and aloe vera.

23. The composite elastic material as claimed in claim 22, wherein the aloe vera constitutes 3% by weight of the at least one silicone elastomer layer and the balance of the skin treatment agents is petroleum jelly, said skin treatment agents constituting up to 20% by weight of the silicone elastomer layer.

24. The composite elastic material as claimed in any one of claims 1–6, wherein the at least one silicone elastomer layer has the following properties:

| | |
|---|---|
| Density: | .5 g/cm$^3$ to 1.3 g/cm$^3$ |
| Tensile Strength: | .1 Pa minimum |
| Durometer (00): | 13–62 |
| 100% Modulus: | 5 kPa to 250 kPa |
| Compression Set: | 0 to 30. |

25. The composite elastic material as claimed in claim 24, wherein the silicone elastomer layer has the following properties:

| | |
|---|---|
| Density: | .94 g/cm$^3$ |
| Tensile Strength: | .5 Pa |
| Durometer (00): | 22 |
| 100% Modulus: | 20 kPa |
| Compression Set: | 8. |

26. The composite elastic material as claimed in claim 7, wherein an interior proximal flange area of said interior wall portion is tapered radially outwardly and an exterior proximal flange area of said posterior wall portion is tapered radially inwardly.

27. The composite elastic material as claimed in claim 8 or 9, including a spherical curved inside distal wall portion of said suction liner, said distal wall portion joining the adjoining interior wall of the suction liner along a tangency that forms a smooth transition between the inside distal wall portion and the adjoining interior wall of the suction liner, and further wherein the adjoining wall of the suction liner is circular in cross-section and has a center of curvature located on said first axis; and further wherein the thickness of the wall of the suction liner adjoining said spherical curved distal wall portion is uniform and equal to the thickness of said anterior wall portion.

28. The composite elastic material as claimed in claim 7, including a second cured silicone elastomer layer between the at least one silicone elastomer layer and the elasticized fabric layer, said second silicone elastomer layer partially penetrating and being embedded in said textile layer on one side thereof so as to form a continuous coating on said one side, and adhered to said at least one silicone elastomer layer on the opposite side of the second silicone elastomer layer.

29. The composite elastic material as claimed in claim 7, wherein the composite elastic material has a minimum tensile strength of one Pa and a 100% modulus of 5 to 30 kPa.

* * * * *